United States Patent
Limaye et al.

(10) Patent No.: US 11,917,998 B2
(45) Date of Patent: Mar. 5, 2024

(54) DISINFECTANT FOR HATCHERIES

(71) Applicant: CEVA SANTE ANIMALE, Libourne (FR)

(72) Inventors: Milind Limaye, Pune (IN); Sadanand Deshpande, Pune (IN)

(73) Assignee: CEVA SANTE ANIMALE, Libourne (FR)

( * ) Notice: Subject to any disclaimer, the term of this patent is extended or adjusted under 35 U.S.C. 154(b) by 0 days.

(21) Appl. No.: 16/639,140

(22) PCT Filed: Aug. 16, 2018

(86) PCT No.: PCT/EP2018/072261
§ 371 (c)(1),
(2) Date: Feb. 14, 2020

(87) PCT Pub. No.: WO2019/034747
PCT Pub. Date: Feb. 21, 2019

(65) Prior Publication Data
US 2020/0205414 A1   Jul. 2, 2020

(30) Foreign Application Priority Data

Aug. 16, 2017 (IN) .............................. 201711028990
Oct. 5, 2017 (EP) ..................................... 17194867
Feb. 16, 2018 (EP) ..................................... 18157268

(51) Int. Cl.
| | |
|---|---|
| *A01N 59/00* | (2006.01) |
| *A01N 25/30* | (2006.01) |
| *A01K 43/00* | (2006.01) |
| *A01K 45/00* | (2006.01) |
| *A01N 37/18* | (2006.01) |
| *A01N 37/36* | (2006.01) |
| *A61L 2/18* | (2006.01) |
| *A01K 41/00* | (2006.01) |
| *A01N 25/34* | (2006.01) |

(52) U.S. Cl.
CPC .............. *A01N 59/00* (2013.01); *A01K 41/00* (2013.01); *A01K 43/005* (2013.01); *A01K 45/007* (2013.01); *A01N 25/30* (2013.01); *A01N 25/34* (2013.01); *A01N 37/18* (2013.01); *A01N 37/36* (2013.01); *A61L 2/18* (2013.01); *A61L 2202/24* (2013.01)

(58) Field of Classification Search
CPC .................................................... A01N 37/16
See application file for complete search history.

(56) References Cited

U.S. PATENT DOCUMENTS

| | | | | |
|---|---|---|---|---|
| 4,521,375 A | * | 6/1985 | Houlsby | A61L 12/124 422/29 |
| 5,462,714 A | * | 10/1995 | Talwalker | A01N 59/12 422/28 |
| 5,891,922 A | * | 4/1999 | Gaumer | A01N 33/12 514/642 |
| 7,291,276 B1 | | 11/2007 | Zahn | |
| 9,701,931 B2 | | 7/2017 | Moore | |
| 2002/0192297 A1 | * | 12/2002 | Ramirez | A61P 31/02 424/605 |
| 2013/0259957 A1 | | 10/2013 | Dagher et al. | |
| 2014/0120179 A1 | | 5/2014 | Smith et al. | |
| 2016/0270389 A1 | * | 9/2016 | Glasbey | A01N 59/00 |
| 2016/0355756 A1 | * | 12/2016 | Krasnansky | C11D 1/8255 |

FOREIGN PATENT DOCUMENTS

| | | |
|---|---|---|
| CN | 103767886 | 5/2014 |
| CN | 106857513 | 6/2017 |
| EP | 2 458 989 | 6/2012 |
| EP | 2 582 236 | 4/2013 |
| WO | WO 2005/112631 | 12/2005 |
| WO | WO 2007/051957 | 5/2007 |
| WO | WO 2007/080453 | 7/2007 |
| WO | WO 2015/066760 | 5/2015 |
| WO | WO 2015/107342 | 7/2015 |
| WO | WO 2017/112425 | 6/2017 |

OTHER PUBLICATIONS

Uptima: sodium acetate, https://www.interchim.fr/ft/0/038086.pdf, Jul. 2016, 2 pages (Year: 2016).*
Written Opinion in International Application No. PCT/EP2018/072261, dated Sep. 19, 2018, pp. 1-6.
Wormwell, F. et al. "Sodium Benzoate and Other Metal Benzoates as Corrosion-Inhibitors in Water and in Aqueous Solutions" *Journal of Applied Chemistry*, Mar. 1952, pp. 150-160, vol. 2, No. 3.
Anonymous "7 Sodium Sulfate Functions in Daily Life—Formula—Uses" *AZ Chemistry*, May 22, 2017, pp. 1-7, obtained from https://azchemistry.com/sodium-sulfate-function.

* cited by examiner

*Primary Examiner* — Kyle A Purdy
(74) *Attorney, Agent, or Firm* — SALIWANCHIK, LLOYD & EISENSCHENK

(57) ABSTRACT

The invention relates to a stable disinfectant composition and the use of said composition for spraying hatching eggs prior to in ovo vaccination, for disinfecting vaccination equipment including vaccination needles, and for flushing vaccination equipment post vaccination cycles.

14 Claims, No Drawings

DISINFECTANT FOR HATCHERIES

CROSS-REFERENCE TO RELATED APPLICATION

This application is the U.S. national stage application of International Patent Application No. PCT/EP2018/072261, filed Aug. 16, 2018.

FIELD OF THE INVENTION

The invention relates to a stable disinfectant composition and the use of said composition for spraying hatching eggs prior to in ovo vaccination, for disinfecting vaccination equipment including vaccination needles, and for flushing vaccination equipment post vaccination cycles.

BACKGROUND OF THE INVENTION

In ovo injection has become an important tool to administer vaccines in the hatcheries. Nevertheless, some basic pre-cautions must be taken into account in order to achieve the best results with this technology. Good sanitation of the hatchery, thorough disinfection/decontamination of the hatching eggs are among these special cares. Furthermore, precise maintenance of the machine is compulsory by way of preventing biofilm generation. By ensuring that these procedures are properly followed, the industry can ensure benefit from this interesting and powerful in ovo vaccination technology.

Chlorine releasing tablets, powders and solutions are the standard disinfection methods in the modern hatchery industry. However, the chlorine release method has the main disadvantage that chlorine is corrosive to several metals and alloys encountered in the hatchery sector and in in ovo vaccination equipment. Moreover, effectiveness of chlorine disinfectants against some microbial pathogens is weakened when organic matter is present.

Hydrogen peroxide ($H_2O_2$) is also commonly used at a concentration of 3% weight/volume. $H_2O_2$ is known to release highly oxidizing nascent oxygen {O} which has strong corrosive action on metal and alloy surfaces apart from being a disinfectant. Handling of stock solutions of $H_2O_2$ is also considered to be risky for the end user on account of the high reactivity of $H_2O_2$ with human skin.

Disinfectant compositions of the prior art cannot be efficiently used in industrial hatcheries because they are two corrosive for the high tech in ovo vaccination equipment, because they are not environmental friendly, because disinfectant compositions are often unstable, because they often cause user safety issues, and because of the limited speed of action against pathogens. Indeed, conventional in ovo vaccination requires killing of the key pathogens found in hatcheries (*E. coli, P. aeruginosa, Salmonella* spp, and *Staphylococcus aureus*) within 3 seconds of exposure which is the average time between two in ovo injection cycles.

Therefore, there is still a need in the industry for a disinfectant composition which is easy to prepare at room temperature prior use, which is free of halogenated chemical compounds, free of aldehydes, which is stable for at least two years in powder or tablet form, which can be solubilized in any tap water within minutes at room temperature, which is stable for at least 6 hours in liquid form, while providing a complete disinfection within three seconds of contact with microbial pathogens. Moreover, said disinfectant composition should not lead to any corrosion of metallic parts of the equipment being sanitized/disinfected, nor provoke any discoloration of the non-metallic parts of the equipment. Furthermore, there is also a need for a composition which, when used as a liquid disinfectant has a broad spectrum of antimicrobial efficacy against the main pathogens found in hatcheries and is safe for human handling.

SUMMARY OF THE INVENTION

Surprisingly, the inventors found that the composition of the present invention overcomes the foregoing problems by providing a stable composition in solid and liquid form, a composition free of halogenated chemical compounds, a composition easily solubilized in tap water and at room temperature, and a composition being effective within 3 seconds while retaining efficacy in a broad range of tap water comprising various salts, being safe to the user, and not leading to any corrosion nor discoloration upon repeated use.

In a first aspect, the aim of the present invention is to provide a stable solid disinfectant composition. A further aspect of the invention is to provide the use of this stable solid composition, after rapid solubilization in tap water, to disinfect eggs in hatcheries prior in ovo vaccination as well as vaccination equipment (injection needles) between every two consecutive in ovo injections during vaccination cycles.

A further object of the present invention is to provide a method of disinfecting eggs and hatchery equipment, including vaccination equipment, comprising the steps of dissolving a stable disinfectant composition in tap water at a concentration of 1 to 5%, and contacting the disinfectant solution for 3 to 5 seconds with surfaces to be treated.

DETAILED DESCRIPTION OF THE INVENTION

In a first aspect, this invention relates, to a stable disinfectant composition comprising:
a. 40 to 50 wt % sodium percarbonate,
b. 20 to 25 wt % tetra acetyl ethylene diamine,
c. 10 to 20 wt % anhydrous citric acid,
d. 0 to 2 wt % alpha olefin sodium sulfonate,
e. 5 to 15 wt % anhydrous sodium acetate,
f. 0.01 to 0.02 wt % of an anti-corrosive agent,
g. 5 to 20 wt % of a filler.

Disinfectants are antimicrobial agents that are applied to the surface of non-living objects to destroy microorganisms that are living on the objects.

As used herein, the term "wt %" means a weight/weight ratio relative to the total weight of the composition.

Sodium percarbonate (CAS 15630-89-4) or peroxy sodium carbonate, or sodium carbonate peroxide, or sodium carbonate peroxyhydrate is an adduct of sodium carbonate and hydrogen peroxide (a perhydrate), with the following formula (2 $Na_2CO_3 \cdot H_2O_2$). It is a colorless, crystalline, hygroscopic and water-soluble solid. Sodium percarbonate is more eco-friendly than sodium perborate commonly used in the industry because it degrades into oxygen, water and sodium carbonate.

Tetra acetyl ethylene diamine (TAED) (CAS 10543-57-4) is a peracetic acid generator. A suitable supplier of TAED is Warwick Chemicals. The TAED may be an uncoated TAED, for example a uncoated powdered form of TAED. A suitable TAED is MykonR B675 TAED.

Alpha olefin sodium sulfonate or sodium $C_{14-16}$ alpha olefin sulfonate surfactants provide outstanding detergent activity with a high compatibility with hard water, and good wetting and foaming properties. It comprises approximately 90 to 95% sulfonic acids, $C_{14-16}$-alkane hydroxy and $C_{14-16}$-alkene, sodium salts with the remaining 5 to 10% Sodium Sulfate. They are available from Parchem.

Anhydrous citric acid is used in the present composition as a pH controller and buffer agent. Anhydrous means that the substance has no or limited amount of water and is in a dry, granulated form.

Anhydrous sodium acetate also abbreviated NaOAc also known as sodium ethanoate, is the sodium salt of acetic acid.

Anti-corrosive agent or corrosion inhibitor is a chemical compound that, when added to a liquid, decreases the corrosion rate of a material, typically a metal or an alloy. Any liquid anti-corrosive agent may be used in the composition of the present invention. Preferred anti-corrosive agent is sodium benzoate.

For the composition according to the present invention, any filler which is highly soluble in water may be used. Preferred filler according to the present invention is the inorganic compound with formula $Na_2SO_4$:sodium sulfate.

The composition according to the present invention preferably comprises:
a. 42 to 48 wt % sodium percarbonate,
b. 22 to 23 wt % tetra acetyl ethylene diamine,
c. 12 to 18 wt % anhydrous citric acid,
d. 0 to 2 wt % alpha olefin sodium sulfonate
e. 8 to 11 wt % anhydrous sodium acetate
f. 0.01 to 0.02 wt % of an anti-corrosive agent,
g. 5 to 11 wt % of a filler.

More preferably, the composition according to the present invention comprises:
a. 44 to 46 wt % sodium percarbonate,
b. 22 to 23 wt % tetra acetyl ethylene diamine
c. 14 to 16 wt % anhydrous citric acid,
d. 0 wt % alpha olefin sodium sulfonate,
e. 9 to 10 wt % anhydrous sodium acetate
f. 0.01 to 0.02 wt % of sodium benzoate,
g. 5 to 8 wt % of sodium sulfate.

In a preferred embodiment, the composition according to the present invention is provided in a solid form including free flowing powder form or tablet. Preferably the composition is in a powder form, and packaged in bags, sachets or pouches. Even more preferably, sachets or pouches are made of water soluble material such as polyvinylalcohol as it is well known to the person skilled in the art.

Prior using the composition as a liquid disinfectant, the composition needs to be dissolved in tap water. Effective concentration of the composition according to the present invention is reached when the composition is dissolved at 1 to 5% concentration in water at room temperature, preferably 2 to 3%. Therefore, for the ease of use, and for safety purposes, unidose packages are provided for predefined amounts of water.

Surprisingly, the present composition when used in powder form was found to dissolve very rapidly in tap water at room temperature within 5 minutes and at very different concentrations of Mg, Ca or Na salts.

Another object of the present invention is to provide the use of a composition comprising:
a. 40 to 50 wt % sodium percarbonate,
b. 20 to 25 wt % tetra acetyl ethylene diamine,
c. 10 to 20 wt % anhydrous citric acid,
d. 0 to 2 wt % alpha olefin sodium sulfonate,
e. 5 to 15 wt % anhydrous sodium acetate,
f. 0.01 to 0.02 wt % of an anti-corrosive agent,
g. 5 to 20 wt % of a filler,
wherein said composition is dissolved in tap water at room temperature at a concentration of 1 to 5 as a disinfectant for spraying eggs prior embryo vaccination, for spraying egg vaccination equipment, and/or for flushing of vaccination equipment. Preferably, the composition is dissolved at a concentration of 2 to 3%.

In ovo vaccination is carried out by machines. These machines perform a number of actions to ensure good vaccination of the chick inside the egg. Benefits of in ovo vaccination include uniformity in mass vaccination, avoidance of bird stress, controlled hygienic conditions, and earlier immunity with less interference from maternal antibodies. However, the entire in ovo vaccination process should be performed in sterile condition so as to prevent any introduction of microbial pathogens and/or contaminants into the eggs.

In a preferred embodiment, the present composition dissolved in water is effective in killing *E. coli, P. aeruginosa, Staphylococcus* spp, *Salmonella*, spp, such as *S. gallinarum*, or *S. enteritidis*.

Another object of the present invention is a method of disinfecting eggs and hatchery equipment, including vaccination equipment, comprising the steps of dissolving a composition comprising:
a. 40 to 50 wt % sodium percarbonate,
b. 20 to 25 wt % tetra acetyl ethylene diamine
c. 10 to 20 wt % anhydrous citric acid,
d. 0 to 2 wt % alpha olefin sodium sulfonate,
e. 5 to 15 wt % anhydrous sodium acetate
f. 0.01 to 0.02 wt % of an anti-corrosive agent,
g. 5 to 20 wt % of a filler,
in tap water at room temperature and at a concentration of 1 to 5%, and contacting the disinfectant solution for 3 to 5 seconds with surfaces to be treated.

All embodiments described above for the stable disinfectant composition also apply to the use of said composition, and to the method of disinfection as described above.

EXAMPLES

Example 1: Stable Disinfectant Composition

| | |
|---|---|
| sodium percarbonate | 45 wt % |
| tetra acetyl ethylene diamine | 22.5 wt % |
| anhydrous citric acid | 15 wt % |
| alpha olefin sodium sulfonate | 1.44 wt % |
| sodium benzoate | 0.016 wt % |
| anhydrous sodium acetate | 9.5 wt % |
| sodium sulfate | 6.55 wt % |

Example 2: Stable Disinfectant Composition

| | |
|---|---|
| sodium percarbonate | 44.5 wt % |
| tetra acetyl ethylene diamine | 23 wt % |
| anhydrous citric acid | 15 wt % |
| alpha olefin sodium sulfonate | 1.44 wt % |
| sodium benzoate | 0.016 wt % |
| anhydrous sodium acetate | 9.5 wt % |
| sodium sulfate | 6.55 wt % |

Example 3: Stable Disinfectant Composition

| | |
|---|---|
| sodium percarbonate | 45.5 wt % |
| tetra acetyl ethylene diamine | 22 wt % |

| | |
|---|---|
| anhydrous citric acid | 15 wt % |
| alpha olefin sodium sulfonate | 1.44 wt % |
| sodium benzoate | 0.016 wt % |
| anhydrous sodium acetate | 9.5 wt % |
| sodium sulfate | 6.55 wt % |

Example 4: Dissolution Rate of the Product of Example 1 Compared to Perasafe Perasafe is a composition of the prior art comprising 50 wt % perboric acid sodium salt, 1 wt % sodium carbonate and 15 wt % citric acid.

Both compositions were mixed at 2% concentration in distilled water, and dissolution visually observed after 5 minutes stirring at 187 rpm. Table 1 shows that the composition according to Example 1 dissolves more efficiently than the disinfectant of the prior art Persafe.

TABLE 1

Comparative dissolution.

| Formulation | Concentration in distilled water | Temperature of water | Rotation speed (rpm) | Observation after 5 mins. | Clarity of solution |
|---|---|---|---|---|---|
| Composition of Example 1 | 2% | 25° C. | 187 | Completely dissolved | Clear |
| PERASAFE | 2% | 25° C. | 187 | Small quantity remains undissolved | Clear |

Example 5: Antimicrobial Efficacy Assays

Antimicrobial efficacy assays were performed with compositions according to Example 1 at 2, 3, and 4% dilution in water.

Material and Methods:

Equipment: Laminar air flow. (ENVAIR), Stop watch, Cyclo mixer (REMI CM 101DX), and Incubator operated at 37° C. (LABTOP)

Chemicals: Sodium meta bisulphite (A.R.) solution (100 mg/ml), Nutrient broth (HIMEDIA) Tested microorganisms: Ps. Aeruginosa (ATCC9027), E. coli (ATCC 8139), S. abony(NCTC 6017), suspensions having count $10^6$ cfu/ml.

Preparation of a 2% liquid solution of the composition of Example 1: Weight accurately 2 g of the composition of Example 1 and dissolve in 100 ml distilled water. Stir sample continuously for about 5 minutes at room temperature until it dissolves completely to obtain a clear solution.

Bactericidal assays: Bactericidal assay were carried out as detailed below.

1 Positive Control

To 8 ml nutrient broth add 100 µl of P. aeruginosa suspension ($10^6$ cfu/ml) and mix well. Incubate at 37° C. for 48 hrs.

After completion of incubation period observe solution for turbidity (bacterial growth).

2 Negative Control

Incubate 8 ml nutrient broth at 37° C. for 48 hrs. After completion of incubation observe solution for turbidity (bacterial growth).

3 Test

To 8 ml 2% composition according to Example 1 solution add 100 µl of P. aeruginosa suspension ($10^6$ cfu/ml) with continuous stirring using cyclo mixer and expose for 3 seconds.

Add 50 µl of neutralizer (100 mg/ml) immediately at the end of 3 seconds to the solution stirring continuously and allow standing for 30 seconds (solution A).

Then transfer 1 ml of solution A to the tube containing 9 ml nutrient broth, mix well and incubate at 37° C. for 48 hrs.

After completion of incubation period observe the solutions for turbidity (bacterial growth). Repeat same procedure for 3% and 4% solution with the composition of Example 1 as well as with the other microbial strains E. coli and S. abony. Results are shown in Table 2:

TABLE 2

Killing efficacy results

| Pathogens at $1 \times 10^6$ cfu/ml | Contact time | % killing efficacy with a solution prepared from composition of Example 1 dissolved in water at: | | |
|---|---|---|---|---|
| | | 2% | 3% | 4% |
| E. coli | 3 seconds | 100 | 100 | 100 |
| P. aeruginosa | 3 seconds | 100 | 100 | 100 |
| S. aureus | 3 seconds | 100 | 100 | 100 |
| S. abony | 3 seconds | 100 | 100 | 100 |

It may be seen from the above results that an exposure for 3 seconds to 2%, 3% and 4% of the composition according to Example 1 in solution exhibits complete killing of E. coli, P. aeruginosa, S.abony, S.aureus (with an individual count $1 \times 10^6$ cfu/ml).

It may therefore be concluded that 2% solution of a solution prepared from the composition of Example 3 is capable of achieving total killing of E. coli, P. aeruginosa, S. abony, S. aureus thereby making it an effective disinfectant for eggs as well as equipment disinfection.

Example 6: Effect of the Water Quality on Stability of the Dissolved Composition and on Killing Efficacy The effect of 4 different water sources was compared for the possible effect on dissolution of the composition at three different dilutions in water at room temperature.

TABLE 3

Effect of water quality on dissolution parameters of the composition according to Example 1. Concentration means the concentration of the dilution of the composition according to Example 1 in water. Hydrogen peroxide and peracetic acid were measured as described in Example 7. Efficacy has been measured against *P. aeruginosa* NCIM 200 cell count $10^6$ cfu/ml with a contact time of 3 seconds. Solubility was assessed at 25° C. and with a rotational speed of 187 rpm. Dissolved means the solution was completely dissolved after 5 minutes observation.

| | | Test parameters | | | | | |
|---|---|---|---|---|---|---|---|
| Concentration | Water quality | Hardness (ppm of CaCO3) | pH of solution | Hydrogen peroxide (ppm) | Peracetic acid (ppm) | Efficacy | Solubility |
| 2% | A | 110 | 7.82 | 1785 | 2105 | 100% Killing | dissolved |
| | B | 305 | 7.93 | 1784 | 2100 | 100% Killing | dissolved |
| | C | 600 | 7.85 | 1784 | 2113 | 100% Killing | dissolved |
| | D | 920 | 7.88 | 1783 | 2089 | 100% Killing | dissolved |
| 3% | A | 110 | 7.89 | 2500 | 3367 | 100% Killing | dissolved |
| | B | 305 | 7.95 | 2495 | 3360 | 100% Killing | dissolved |
| | C | 600 | 7.87 | 2505 | 3345 | 100% Killing | dissolved |
| | D | 920 | 7.88 | 2506 | 3354 | 100% Killing | dissolved |
| 4% | A | 110 | 7.86 | 3034 | 3903 | 100% Killing | Dissolved |
| | B | 305 | 7.97 | 3025 | 3889 | 100% Killing | dissolved |
| | C | 600 | 7.83 | 3033 | 3901 | 100% Killing | dissolved |
| | D | 920 | 7.87 | 3099 | 3900 | 100% Killing | dissolved |

As shown above, water quality has no significant effect on the speed of solubilization of the composition according to Example 1. Furthermore, we have also shown that the water quality has no effect on the antimicrobial efficacy following 3 seconds of exposure.

Example 7: Stability Studies of the Solid Composition According to the Invention Materials and Methods:

The following equipment has been used: Stability chambers having Temperature and Humidity control; Magnetic stirrer (REMI 2 ML); and pH Meter (WAVETEK 5000).

The following chemicals have been used: Standard 0.1M Potassium permanganate(A.R.) solution; Standard 0.1 M Sodium thioslphate(A.R.) solution; Dilute sulphuric acid; Potassium Iodide solution(A.R.); 10% Distilled water.

Experimental Conditions:

| Temperature | 30° C. |
|---|---|
| Humidity | 75% |
| Testing intervals | Initial, 1, 2, 3, 4, 5, 6 month |
| Temperature | 40° C. |
| Humidity | 75% |
| Testing intervals | Initial, 1, 2, 3, 4, 5, 6 month |

Preparation of 2% solution from the composition of Example 1: 2 g of the composition of Example 1 were dissolved in 100 ml distilled water. Sample was stirred continuously until complete dissolution to obtain clear solution. (Solution 1)

Estimation of Peracetic Acid and Hydrogen Peroxide:

50 ml dilute sulphuric acid were transferred to the 250 ml Iodine flask. 25 ml of above prepared solution 1 were transferred to the flask followed by stirring. Titrate above solution using 0.1 M potassium permanganate solution until slight pink color appears to the solution. Note burette reading (A).

Add immediately 10 ml 10% potassium iodide solution to the flask.

Liberated iodine is then titrated using 0.1 M sodium thiosulphate solution until solution become colorless. Note burette reading (B).

Calculation:

Hydrogen Peroxide (ppm)=Burette reading(A)×0.0085× Actual molarity of KMnO4 solution×1000×1000 divided by the volume of sample (ml)×standard molarity of $KMnO_4$ solution (Each ml of 0.1 M $KMnO_4$ solution equivalent to 0.0085 gm hydrogen peroxide)

Peracetic acid (ppm)=Burette reading (B)×0.0038×Actual molarity of Sodium thiosulphate solution×1000×1000 divided by the volume of sample (ml)×standard molarity of Sodium thiosulphate solution.

(Each ml of 0.1 M sodium thiosulphate solution equivalent to 0.0038 gm peracetic acid)

Table 4 shows the stability data of the composition according to Example 1 as assessed by preparing a 2% dilution in water, and assessing the pH of the solution, its peracetic acid content, as well as the hydrogen peroxide content following storage of the powder for 0 to 6 month at temperatures of 30° C. or 40° C.

TABLE 4 shows the stability data of the composition according to Example 1.

| Time (month) | Temperature | Description | pH | Peracetic acid content (ppm) | Hydrogen peroxide content |
|---|---|---|---|---|---|
| | | | | Data form a 2% solution | |
| 0 | 30° C. | White powder | 8.10 | 2200 | 1785 |
| | 40° C. | White powder | 8.10 | 2200 | 1785 |
| 1 | 30° C. | White powder | 7.80 | 2113 | 1933 |
| | 40° C. | White powder | 7.80 | 2228 | 1708 |
| 2 | 30° C. | White powder | 7.80 | 2100 | 1889 |
| | 40° C. | White powder | 7.80 | 2125 | 1700 |
| 3 | 30° C. | White powder | 7.78 | 2120 | 1782 |
| | 40° C. | White powder | 7.82 | 2028 | 1754 |
| 4 | 30° C. | White powder | 7.98 | 2105 | 1701 |
| | 40° C. | White powder | 7.80 | 2066 | 1725 |
| 5 | 30° C. | White powder | 7.82 | 2107 | 1738 |
| | 40° C. | White powder | 7.80 | 2089 | 1733 |

Furthermore, the stability of a composition according to Example 1 after dilution in water at 2, 3, or 4% has been followed for 6 hours according to the method described above. The results (Table 5) show the solution is stable for at least 6 hours.

TABLE 5

Stability of the composition according to Example 1 in solution.

| Concentration of Composition of Example 1 in solution at: | Time | Appearance | pH of solution | Peracetic acid (ppm) | Hydrogen Peroxide (ppm) |
|---|---|---|---|---|---|
| 2% | 0 hour | Clear | 7.82 | 2105 | 1785 |
|  | 4 hours | Clear | 7.93 | 2065 | 1785 |
|  | 6 hours | Clear | 8.11 | 2013 | 1755 |
| 3% | 0 hour | Clear | 7.70 | 3367 | 2500 |
|  | 4 hours | Clear | 7.80 | 3167 | 2495 |
|  | 6 hours | Clear | 7.96 | 3054 | 2455 |
| 4% | 0 hour | Clear | 7.70 | 3903 | 3034 |
|  | 4 hours | Clear | 7.92 | 3888 | 2956 |
|  | 6 hours | Clear | 8.26 | 3445 | 2847 |

TABLE 6

Stability of the killing activity. 100% means 100% killing efficacy. 3" and 5" means 3 seconds and 5 seconds contact with the composition according to Example 1 at 2, 3 and 4% concentration, respectively.

| Composition according to Example 1 in solution at: | Stage | 0 hour | | 4 hours | | 6 hours | |
|---|---|---|---|---|---|---|---|
| | | 3" | 5" | 3" | 5" | 3" | 5" |
| 2% | E. coli NCIM 2065 | 100% | 100% | 100% | 100% | 100% | 100% |
| | P. aeruginosa NCIM 2200 | 100% | 100% | 100% | 100% | 100% | 100% |
| | S. abony NCIM 2257 | 100% | 100% | 100% | 100% | 100% | 100% |
| | S. aureus NCIM 2079 | 100% | 100% | 100% | 100% | 100% | 100% |
| 3% | E. coli NCIM 2065 | 100% | 100% | 100% | 100% | 100% | 100% |
| | P. aeruginosa NCIM 2200 | 100% | 100% | 100% | 100% | 100% | 100% |
| | S. abony NCIM 2257 | 100% | 100% | 100% | 100% | 100% | 100% |
| | S. aureus NCIM 2079 | 100% | 100% | 100% | 100% | 100% | 100% |
| 4% | E. coli NCIM 2065 | 100% | 100% | 100% | 100% | 100% | 100% |
| | P. aeruginosa NCIM 2200 | 100% | 100% | 100% | 100% | 100% | 100% |
| | S. abony NCIM 2257 | 100% | 100% | 100% | 100% | 100% | 100% |
| | S. aureus NCIM 2079 | 100% | 100% | 100% | 100% | 100% | 100% |

Example 8: Antimicrobial Efficacy

A 2% solution from the composition of Example 1 has been prepared as follows: 2 g of the composition of Example 1 were dissolved in 100 ml distilled water. Sample was stirred continuously until complete dissolution to obtain clear solution (Solution A).

To 5 ml aliquot of Solution A, 0.1 ml of bacterial culture having a density of approximately $10^6$ cfu/ml was added and kept at a temperature between 18 and 20° C. with intermittent shaking. After different time intervals (Killing/Innactivation contact time of 5, 10 or 60 seconds), a loopfull was added in a test tube containing sterile nutrient broth for bacterial cultures, and sterile Sabouraud broth for fungal spp. Then all the nutrient broth tubes were incubated at 37° C. for 48 hours, while Sabouraud broth tubes were incubated at room temperature in the dark for 72 hours to observe growth or inactivation.

The results obtained are summarized in Table 7.

TABLE 7

N means no viable organisms have been observed; V means organisms were observed. MRSA means the strain is a multi-resistant S. aureus.

| | Viability/Inhibition after a contact time of: | | |
|---|---|---|---|
| Test microorganism | 5 Sec. | 10 Sec. | 60 Sec. |
| E. coli (ATCC 25922) | N | N | N |
| S. typhimurium (NCTC 786) | N | N | N |
| P. aeruginosa (Fisher's immunotype IV) | N | N | N |
| S. aureus (ATCC 25923- MRSA) | N | N | N |
| C. albicans (ATCC 10231) | N | N | N |
| A. Niger (ATCC-16404) | V | N | N |

This data confirms the speed of kill of the composition according to the present invention.

Example 9: Stable Disinfectant Composition

| | |
|---|---|
| sodium percarbonate | 45 wt % |
| tetra acetyl ethylene diamine | 22.5 wt % |
| anhydrous citric acid | 15 wt % |
| sodium benzoate | 0.016 wt % |
| anhydrous sodium acetate | 9.5 wt % |
| sodium sulfate | 6.55 wt % |

The stability of a composition according to Example 9 after dilution in water at 2, or 4% has been followed for 6 hours according to the method described above. The results (Table 8) show the solution is stable for at least 6 hours.

TABLE 8

| Concentration of Composition of Example 9 in solution at: | Time | Appearance | pH of solution | Peracetic acid (ppm) | Hydrogen Peroxide (ppm) |
|---|---|---|---|---|---|
| 2% | 0 hour | Clear | 7.32 | 2209 | 1798 |
|  | 4 hours | Clear | 7.39 | 2189 | 1785 |
|  | 6 hours | Clear | 7.40 | 2103 | 1785 |
| 4% | 0 hour | Clear | 7.32 | 3922 | 3036 |
|  | 4 hours | Clear | 7.39 | 3898 | 2965 |
|  | 6 hours | Clear | 7.40 | 3500 | 2879 |

The invention claimed is:

1. A stable disinfectant composition, wherein the composition stable disinfectant composition is a solid composition and comprises:
   a) 42 to 48 wt % sodium percarbonate;
   b) 22 to 23 wt % tetra acetyl ethylene diamine;
   c) 12 to 18 wt % anhydrous citric acid;
   d) 0 to 2 wt % alpha olefin sodium sulfonate;
   e) 8 to 11 wt % anhydrous sodium acetate;
   f) 0.01 to 0.02 wt % of an anti-corrosive agent; and
   g) 5 to 11 wt % of a filler.

2. The stable disinfectant composition according to claim 1, wherein the filler is sodium sulfate.

3. The stable disinfectant composition according to claim 1, wherein the anti-corrosive agent is sodium benzoate.

4. The stable disinfectant composition according to claim 1, wherein the composition comprises:
   a) 44 to 46 wt % sodium percarbonate;
   b) 22 to 23 wt % tetra acetyl ethylene diamine;
   c) 14 to 16 wt % anhydrous citric acid;
   d) 0 wt % alpha olefin sodium sulfonate;
   e) 9 to 10 wt % anhydrous sodium acetate;
   f) 0.01 to 0.02 wt % of sodium benzoate; and
   g) 5 to 8 wt % of sodium sulfate.

5. The stable disinfectant composition according to claim 1, wherein the composition is in a tablet form.

6. The stable disinfectant composition according to claim 1, wherein the composition is packaged in a sachet or a pouch.

7. The stable disinfectant composition according to claim 1, wherein the composition is packaged in a sachet or a pouch and wherein the sachet or the pouch is made of water-soluble material.

8. A stable liquid disinfectant composition comprising the stable disinfectant composition according to claim 1 dissolved in water at a dilution of 1 to 5%.

9. The liquid composition according to claim 8, wherein the composition is a disinfectant for spraying eggs prior embryo vaccination, for spraying egg vaccination equipment, and/or for flushing of vaccination equipment.

10. The liquid composition according to claim 8, wherein the composition is dissolved in tap water at room temperature and at a dilution of 2 to 3%.

11. The liquid composition according to claim 8, which is a disinfectant which is effective in killing *E. coli, P. aeruginosa, Staphylococcus* species and/or *Salmonella* species.

12. A method of disinfecting eggs comprising the steps of dissolving a composition according to claim 1, in tap water at room temperature and at a concentration of 1 to 5%, and contacting the disinfectant solution for 3 to 5 seconds with the surfaces of said eggs.

13. A method of disinfecting hatchery equipment comprising the steps of dissolving a composition according to claim 1, in tap water at room temperature and at a concentration of 1 to 5%, and contacting the disinfectant solution for 3 to 5 seconds with surfaces of said hatchery equipment.

14. A method of disinfecting vaccination equipment comprising the steps of dissolving a composition according to claim 1, in tap water at room temperature and at a concentration of 1 to 5%, and contacting the disinfectant solution for 3 to 5 seconds with surfaces of vaccination equipment.

\* \* \* \* \*